US00PP20093P3

(12) United States Plant Patent
Yates

(10) Patent No.: US PP20,093 P3
(45) Date of Patent: Jun. 9, 2009

(54) *BEGONIA* PLANT NAMED 'YABOS'

(50) Latin Name: *Begonia boliviensis*
Varietal Denomination: YABOS

(76) Inventor: Frederic C. Yates, Holmes Chapel Rd., Somerford, Congleton Cheshire (GB), CW12 4SP ( * ) Notice: Subject to any disclaimer, the term of this patent is extended or adjusted under 35 U.S.C. 154(b) by 452 days.

(21) Appl. No.: 11/445,753

(22) Filed: Jun. 2, 2006

(65) Prior Publication Data

US 2007/0283473 P1 Dec. 6, 2007

(51) Int. Cl.
*A01H 5/00* (2006.01)

(52) U.S. Cl. ..... Plt./343

(58) Field of Classification Search ..... Plt./343
See application file for complete search history.

*Primary Examiner*—Kent Bell
(74) *Attorney, Agent, or Firm*—Penny J. Aguirre

(57) ABSTRACT

A new cultivar of *Begonia, Begonia boliviensis* 'Yabos', characterized by its compact, freely branched, pendulant plant habit combined with red-orange flowers and ease of propagation.

2 Drawing Sheets

Botanical classification: *Begonia boliviensis.*
Cultivar designation: 'Yabos'.

BACKGROUND OF THE INVENTION

The present invention relates to a new and distinct cultivar of *Begonia* plant, botanically known as *Begonia boliviensis* 'Yabos' and will be referred to hereafter by its cultivar name, 'Yabos'.

The new cultivar was derived from a controlled breeding program conducted by the inventor at his nursery in Congleton, Cheshire, U. K. The overall purpose of the breeding program is to make selections of *Begonia* plants with compact plant habits suitable for container use combined with superior flower performance and productive stock plants for propagation. 'Yabos' was selected as a whole plant in 2004 and derived from a cross made between unnamed proprietary plants of *Begonia boliviensis.*

'Yabos' was selected as unique for its compact pendulous plant habit, its abundant production of side shoots and its red-orange flowers. 'Yabos' differs from its closest comparison cultivar, 'Bonfire' (U.S. Plant Pat. No. 15,108) in having a flatter, more pendulous plant habit and flowers that are more red in color.

Asexual reproduction of the new cultivar was first accomplished by terminal stem cuttings in Congleton, Cheshire, U. K. in 2004 by the inventor. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Yabos' as a new and distinct cultivar of *Begonia.*

1. 'Yabos' exhibits a compact, pendulous plant habit.
2. 'Yabos' readily produces side shoots.
3. 'Yabos' exhibits red-orange flowers.

4. 'Yabos' produces productive stock plants for propagation.

BRIEF DESCRIPTION OF THE DRAWING

The accompanying colored photographs illustrate the overall appearance and distinct characteristics of the new *Begonia.* The photographs were taken in July of a plant approximately 17 weeks in age as grown in a one-liter container in Swavesey, Campbridgeshire, U. K.

The photograph in FIG. 1 provides a side view of 'Yabos' in bloom.

Figure 1:
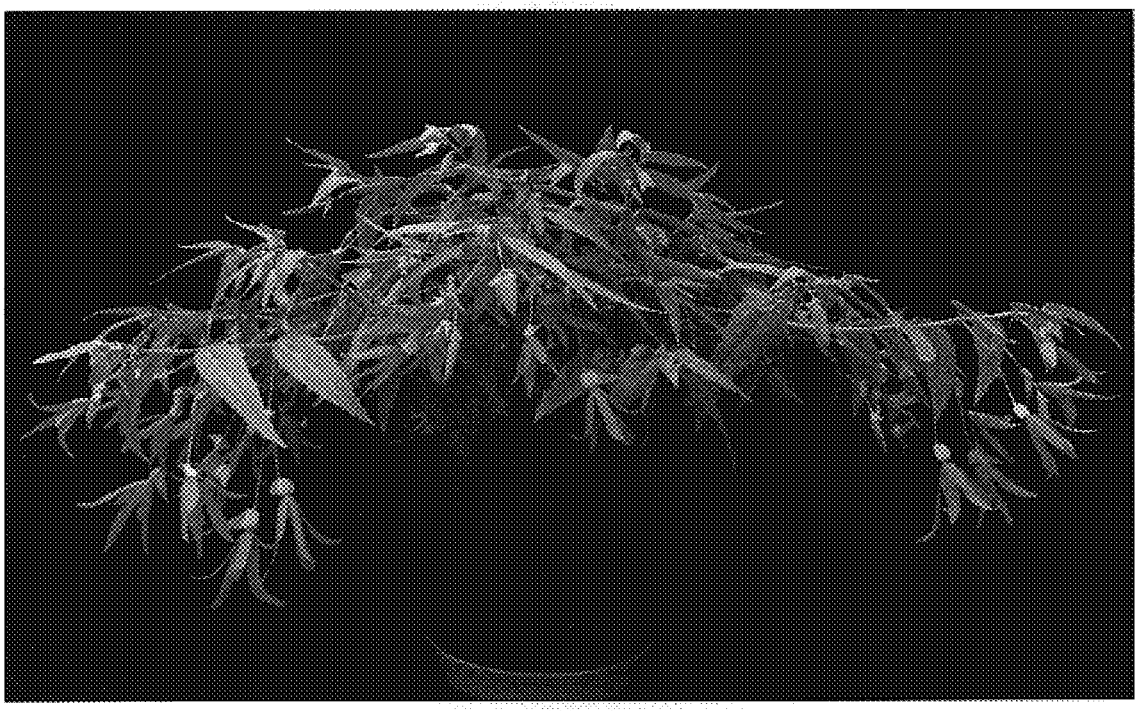
Figure 2:
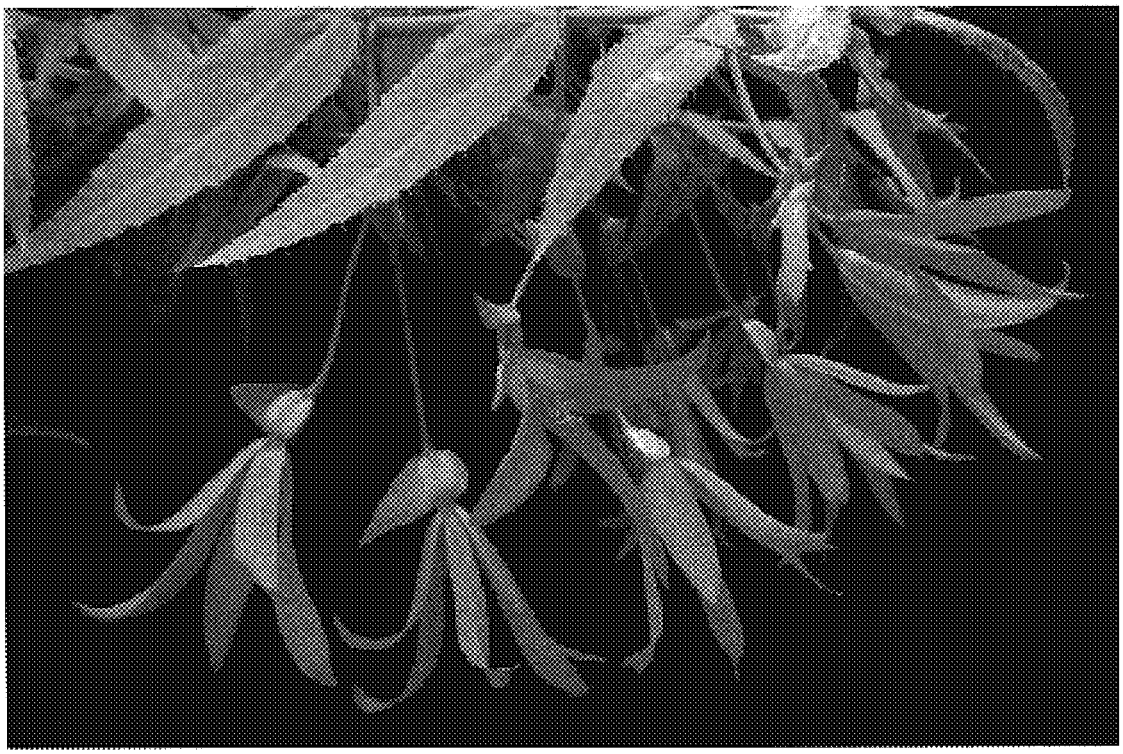

The photograph in FIG. 2 provides a close-up view of the flowers of 'Yabos'. The colors in the photographs are as close as possible with the photographic and printing technology utilized.

The color values cited in the detailed botanical description accurately describe the colors of the new *Begonia.*

DETAILED BOTANICAL DESCRIPTION OF THE PLANT

The following is a detailed description of plants of the new cultivar approximately 17 weeks in age as grown in one liter containers under greenhouse conditions with ambient light in Congleton, Cheshire, U. K. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Yabos' is a cultivar of *Begonia boliviensis.*
Parentage: Selection from unnamed proprietary selections of *Begonia boliviensis.*
General plant characteristics:
*Plant type.*—Deciduous tuberous perennial, grown primarily for use in baskets and containers.

*Plant habit.*—Compact, prostrate and pendulous.

*Flowering period.*—From late March to November.

*Height and spread.*—Reaches about 20 cm in height and about 60 cm in spread.

*Cold hardiness.*—USDA Zone 10.

*Culture.*—Grows in any commercial soil or growing media, 12 hours of light is needed for production in the winter months.

*Diseases and pests.*—No susceptibility or resistance to diseases or pests has been observed.

*Root description.*—Fleshy to fibrous with tubers produced for over-wintering.

*Tubers.*—Oblate in shape, average of 4.5 cm in diameter (larger on older plants), surface is smooth and slightly corky, color between 199C and 199D.

Growth and propagation:

*Growth rate.*—Typical vigor for the species but with more compact growth.

*Propagation.*—Terminal stem cuttings.

*Time required for root development.*—10 to 14 days at 22° C.

*Time required for root development.*—5 weeks to reach commercial size.

Stem description:

*Stem size.*—Average of 35 cm in length and 1 cm in width with lateral branches about 4 mm in width.

*Stem shape.*—Round, solid.

*Stem color.*—197B.

*Stem surface.*—Smooth, glabrous but glaucous, lenticels absent.

*Internode length.*—Average of 2.3 cm.

*Branching habit.*—Freely branched.

*Branching angle at emergence.*—About 45°.

Foliage description:

*Leaf shape.*—Lanceolate, asymmetric with one side wider than the other.

*Leaf division.*—Simple.

*Leaf base.*—Rounded on narrower side, cordate on wider side.

*Leaf apex.*—Acuminate.

*Leaf venation.*—Pinnate, color between 139A and 147A on upper surface and 146B on lower surface.

*Leaf margins.*—Serrate with sharp bristles emerging from tips of the teeth.

*Leaf attachment.*—Petiolate.

*Leaf arrangement.*—Alternate.

*Leaf surface.*—Upper surface; glabrous, smooth, lower surface; glabrous on blade and very weakly pubescent along veins.

*Leaf color.*—Upper surface; between 139A and 147A, lower surface; closest to 191A.

*Leaf size.*—Average of 7.7 cm in length and 2.6 cm in width.

*Leaf quantity.*—Average of 14 per branch.

*Leaf fragrance.*—None.

*Petioles.*—About 1 cm in length and 2 mm in width, surface is very sparsely pubescent with simple hairs, color is nearest 197C.

*Stipules.*—Triangular in shape, 177C in color and rapidly becoming dry and papery, about 3 mm in length and width.

Female flowers:

*Pedicels.*—About 3.2 cm in length and 1 mm in width, 35A in color, pubescence absent.

*Flower buds.*—Flattened ovate in shape, about 2.2 cm in length and 6 mm in width, between 33A and N34A in color.

*Flower size.*—About 3.3 cm in length and 4.1 cm in width.

*Tepals.*—4 in number, narrow ovate in shape, recurved near the apex, acute to acuminate apex, rounded to cuneate base, average of 3.6 cm in length and 6 mm in width, glabrous and smooth surface, entire margin, inner and outer surfaces are between N30A and N30B in color.

*Corolla form.*—Spreading, tetals are un-fused.

*Styles.*—3 in number, cylindrical, connate for basal 1 mm, about 7 mm in length and <1 mm in width, 40A in color.

*Stigmas.*—Bifid in shape, lobes about 2 mm in length and <1 mm in width, 26B in color.

*Ovaries.*—Inferior, about 8 mm in length and 5 mm in width (excluding wings), color is 139D tinged with 35A (especially on the wings).

*Seed.*—Very numerous, to small to measure, nearest to 164A in color.

What is claimed is:

1. A new and distinct cultivar of *Begonia* plant named 'Yabos' as herein illustrated and described.

* * * * *